(12) United States Patent
Thierry-Palmer et al.

(10) Patent No.: US 7,888,000 B2
(45) Date of Patent: Feb. 15, 2011

(54) METHOD FOR IDENTIFYING SALT-SENSITIVE PERSONS

(75) Inventors: Myrtle Thierry-Palmer, Decatur, GA (US); Akins Doherty, Lithonia, GA (US); Keri J. Griffin, LaGrange, GA (US); Mohamed A. Bayorh, Stone Mountain, GA (US)

(73) Assignee: Morehouse School of Medicine, Atlanta, GA (US)

( * ) Notice: Subject to any disclaimer, the term of this patent is extended or adjusted under 35 U.S.C. 154(b) by 0 days.

(21) Appl. No.: 10/617,254

(22) Filed: Jul. 11, 2003

(65) Prior Publication Data

US 2004/0072374 A1 Apr. 15, 2004

Related U.S. Application Data

(60) Provisional application No. 60/395,457, filed on Jul. 12, 2002.

(51) Int. Cl.
*C07J 9/00* (2006.01)
*C12Q 1/00* (2006.01)

(52) U.S. Cl. .................... 435/4; 552/541; 552/653; 540/120

(58) Field of Classification Search .................... 435/4; 552/541, 653; 540/120
See application file for complete search history.

(56) References Cited

U.S. PATENT DOCUMENTS

| | | | | |
|---|---|---|---|---|
| 3,772,150 A | * | 11/1973 | Norman et al. | 435/155 |
| 4,269,777 A | * | 5/1981 | De Luca et al. | 552/541 |
| 4,883,791 A | * | 11/1989 | Pak et al. | 514/167 |
| 5,202,266 A | | 4/1993 | Nakagawa et al. | |
| 5,989,854 A | * | 11/1999 | Cook | 435/35 |
| 6,010,861 A | * | 1/2000 | Blume | 435/7.1 |
| 6,054,282 A | * | 4/2000 | Garman | 435/7.2 |
| 6,610,504 B1 | * | 8/2003 | Yuan | 435/15 |

FOREIGN PATENT DOCUMENTS

| | | |
|---|---|---|
| WO | WO 99/67211 A | 12/1999 |
| WO | WO 02/46746 A | 6/2002 |
| WO | WO 02/057797 A | 7/2002 |

OTHER PUBLICATIONS

Thierry-Palmer, M, et al:"Plasma 25-hydroxyvitamin D concentrations are inversely—salt-sensitive rats." J. Steroid Biochem ol. Biol. 1998;66:255-61.

Wu, et al.:"Regulation of Sodium, Calcium and Vitamin D—"Clin. Exp. Pharmacol Physiol 200/27:378-83.

Thierry-Palmer, Myrtle et al., "Dahl salt-sensitive rats excrete—". J. Nurtrition 2003;133:187-190.

* cited by examiner

*Primary Examiner*—Leon B Lankford
(74) *Attorney, Agent, or Firm*—Ping Wang; Andrews Kurth, LLP

(57) ABSTRACT

Salt sensitivity is measured as a function of the urinary 25-OHD binding activity, which may be evaluated by measuring 25-hydroxyvitamin D binding activity using radiolabeled 25-hydroxyvitamin $D_3$. High binding activity is indicative of salt sensitivity and is an important predictor for development of salt-sensitivity related hypertension.

3 Claims, No Drawings

METHOD FOR IDENTIFYING SALT-SENSITIVE PERSONS

This application takes priority from Provisional Patent Application No. 60/395,457 filed Jul. 12, 2002.

This invention was partially funded under grant #SO2 82048 by the National Institutes of Health, MBRS. Hence, the United States Government has certain rights in this invention.

FIELD OF THE INVENTION AND BACKGROUND INFORMATION

This invention relates to evaluation of salt sensitivity as it relates to propensity to develop hypertension.

It is estimated that 25% of the U.S. population is salt-sensitive, responding to high salt intake with an increase in blood pressure. 25-Hydroxyvitamin D, a liver metabolite, is the precursor of the hormonal form of vitamin D, 1,25-dihydroxyvitamin D (1,25-$(OH)_2$D), which is synthesized in the kidney. Previously it was demonstrated that an inverse association can be found between plasma 25-hydroxyvitamin D (25-OHD) concentration and blood pressure in Dahl salt-sensitive (S) rats during high salt intake. Plasma 25-OHD concentration of S rats decreased with days fed a high salt diet, as blood pressure increased. Spontaneously hypertensive rats do not have low plasma 25-OHD concentrations, suggesting that reduction of plasma 25-hydroxyvitamin D concentration may be specific to salt-induced hypertension.

It is also now known that exogenous 25-OHD will not attenuate the blood pressure increase in S rats fed a high salt diet, nor will exogenous 25-OHD increase plasma 25-OHD concentration, suggesting a higher rate of metabolism and/or clearance of 25-OHD when S rats are fed a high salt diet.

Elderly hypertensive females with low plasma renin activity, characteristic of salt-induced hypertension, were reported to have significantly lower plasma 25-OHD concentrations compared with normotensive elderly and young females. Black Americans have a higher rate of salt-sensitive than white Americans, and a higher rate of hypertension. Black Americans have been shown to have significantly lower mean plasma 25-OHD concentrations compared with white Americans in several studies involving both males and females and in a report based on the third National Health and Nutrition Examination Survey (NHANES III, 1988-91). The NHANES III study comprised 18,875 adolescents and adults. Prevalence of low 25-OHD values (less than 10 ng/ml) was greater in non-Hispanic blacks than in non-Hispanic whites.

Low levels of 25-OHD in black Americans have been ascribed, in part, to reduced epidermal vitamin D photosynthesis associated with high melanin skin content. The lower mean plasma 25-OHD concentrations found for black subjects in the studies might also be affected by lower plasma 25-OHD concentrations in a subset of salt-sensitive black subjects with borderline or moderately high blood pressure. In a study of matched pre-menopausal females without history of hypertension, mein serum concentration of 25-OHD was slightly, but not significantly, lower in the 70 black subjects compared with the 67 white subjects. Young Dahl S rats fed a low salt diet exhibit plasma 25-OHD concentrations slightly, but not significantly, lower than that of R rats.

Based on the blood pressure change in response to a salt load, a previous report found 18% and 37% salt sensitivity for 18-23 year-old Caucasian and African-American subjects, respectively. Another report found 22% prevalence of salt sensitivity in 140 African-American adolescents.

SUMMARY OF THE INVENTION

It is the purpose of this invention to find an economical, non-intrusive and rapid means of identifying salt-sensitive persons who may have or can be expected to develop hypertension based on salt sensitivity. Salt sensitivity is measured as a function of the urinary 25-OHD binding activity, which may be evaluated by (1) collecting a urine sample from an individual, (2) preparing samples containing a known amount of radiolabeled 25-hydroxyvitamin $D_3$, (3) dividing the samples obtained in step (2) into two sets. To the first set of samples obtained in step (2) is added a known amount of 25-hydroxyvitamin $D_3$ (designated 25-OHD samples) and to the second set of samples obtained in step (2) there is no addition of 25-hydroxyvitamin $D_3$ (designated non-25-OHD samples). All samples are then incubated and the amount of radioactivity in each sample is measured. The amount of activity in any urine sample is obtained by subtracting the count of activity in 25-OHD samples from the amount of activity in the samples to which no 25-OHD (non25-OHD) has been added, to obtain specific binding. High binding activity is indicative of salt sensitivity.

DESCRIPTION OF THE INVENTION

It has now been found that S (salt-sensitive) rats excrete 25-OHD and their urine has 25-OHD binding activity. This binding activity is markedly increased during high salt intake. In one set of studies, at week 2 of low salt intake, female S rats excreted 11±3 ng 25-OHD/24 hours into the urine, but excretion by Dahl salt resistant (R) female rats was non-detectable. At week 2 of high salt intake, female S rats excreted four times the amount of 25-OHD as compared to the female R rats. Vitamin D binding activity in the urine of female S rats was 22 times that found in the urine of female R rats at week 2 of low salt intake and about 40 times that found in the urine of R rats at week 2 of high salt intake, when female S rats were hypertensive. Attempts to increase plasma 25-OHD by administering 25-hydroxycholecalciferol via osmotic pumps were successful in S rats fed low, but not high, salt diets. Hence, it is found that urinary 25-OHD binding activity and/or 25-OHD levels can be used to serve as an indicator for salt sensitivity. Urinary 25-OHD binding activity could serve as a marker of salt-sensitivity in normotensive individuals as well as in hypertensive individuals and during both high and low salt intake. The predictive value of this test could be very important in prevention and early treatment of hypertension related to salt sensitivity.

At present, determination of salt sensitivity is not a routine procedure. Estimates of salt-sensitivity in the research setting have been based on the change of blood pressure in response to a change in salt intake (from high to low or from low to high). This method has not always proved useful, because of the very small change (>5 mm Hg) and the variability of blood pressure in an individual. There is also an association between low renin levels and salt-induced hypertension, but this relationship is not strong enough for use in routine diagnosis.

It is now possible, using methods of the invention, to perform tests to distinguish salt-sensitive individuals from salt-insensitive individuals by evaluation of levels of 25-OHD binding activity and/or evaluation of 25-OHD in the urine. One aspect of the invention is the provision of kits for use in evaluating salt sensitivity by measuring 25-OHD binding activity in the urine. Prior art used to evaluate 25-OHD level in the plasma required 25-OHD radiolabelled 25-OHD, a binding protein or antibodies to 25-OHD. The present evaluative tool uses, as specialized reagents, only the radiolabeled 25-OHD$_3$ (Amersham, Corporation, Arlington Heights, Ill.) and the unlabeled 25-hydroxyvitamin D$_3$. All other materials used in testing are commonly available in laboratories doing testing for clinical evaluations.

The present invention offers several advantages over the prior art methods. First, it is much easier to obtain urine than blood, since such collection does not require use of sterile technique by a professional. Secondly, no expensive protein is required for use in testing. Both of these factors result in decrease in price and inconvenience. Kits for use in the methods of the invention may contain, as reagents, labeled 25-OHD$_3$ and unlabeled 25-OHD$_3$ along with instructions for use in measuring salt sensitivity. In such kits, it would not be necessary to have antibodies to 25-OHD.

Materials and Methods

Animal Diets: Four to five week old Dahl salt-sensitive (SS/JR) and salt resistant (SR/Jr) female rats (100-110 g) were obtained from Harlan Sprague Dawley (Indianapolis, Ind.). The rats were allowed free access to water and a non-purified diet (Purina, LabDiet 5001, PMI Nutritional International, Inc, Brentwood, Mo.). They were housed in a room with 12 hour light/dark cycles and, after one week of acclimation, were divided into groups of six rats each and fed either a low (3 g/kg) or high (80 g/kg) salt diet for two weeks. The rats were placed in metabolic cages at baseline and on the seventh day of each week a 24 hour urine collection was made. Urine was stored at −80° C. At the termination of the dietary treatments, rats were anesthetized (ketamine-zylazine, 44/10 mg/kg body weight) and blood was drawn by heart puncture into heparinized tubes. Plasma was obtained by centrifuging the blood at 1,500 g for 10 minutes. Rats were sacrificed by sodium pentobarbital overdose.

Materials: The 25-hydroxycholecalciferol (25-OHD$_3$) was purchased from ICN (Costa Nesa, Calif.). The concentration of 25-OHD$_3$ dissolved in ethanol was determined by ultraviolet spectroscopy at 265 nm using a Lambda 3B spectrophotometer and a molar absorption coefficient of 18,200 mol/L$^{-1}$cm$^{-1}$. Organic solvents were analytical or HPLC grade.

25-Hydroxyvitamin D concentration: 25 Hydroxy[26(27) methyl-$^3$H]cholecalciferol was purified on a 0.46×25 cm Zorbax-Sil HPLC column with dichloromethane-isopropanol (95/5, v/v) at a flow rate of 1 ml/min. Synthetic 25-OHD$_3$ served as standard.

25 Hydroxyvitamin D was isolated from 3 ml urine by dichloromethane/methanol liquid-liquid extraction followed by solid-phase separation on silica cartridges. The fraction containing 25 OHD was purified by HPLC methods. Radiolabeled 25-OHD$_3$ (13 Bq) was added to the plasma and urine samples prior to purification to determine recovery. Protein binding assay kits containing rat vitamin D binding protein (Nichols Institute Diagnostics, San Juan Capistrano, Calif.) were used to assay the 25 OHD peaks. Standard curves were constructed using 25-OHD$_3$ (0.039, 0,078, 0.156, 0,312, 0.625, 1.25 and 25 ng/tube). The limit of detection of the assay, as designed, was 0.16 nmol/L for urine and 0.98 nmol/L for plasma.

25-hydroxyvitamin D binding activity: Urine was tested for specific binding to 25-OHD$_3$ by modification of the method of Reinhardt and Hollis (Methods in Enzymol. 123: 176-185 (1986)) and the assay procedure for 25-OHD of Nichols Institute Diagnostics. Urine samples were diluted with 0.1 mol/L boric acid buffer, pH 8.6 (5-10 fold dilution). Aliquots of the diluted urine samples (0.5 ml) were incubated with radiolabeled 25-OHD$_3$ (0.58 nmol/L, 167 Bq) in the presence of ethanol or 200 fold excess unlabeled 25-OHD$_3$. Ligands were added in 10-20 μL ethanol. Incubation was at 4° C. for 2 hours. A dextran-coated charcoal preparation (0.2 ml) was added to each incubation mixture and incubation was continued for 20 minutes at 4° C. The dextran-coated charcoal contained 12 g/L charcoal, 1.2 g/L Dextran T-70, and 0.5 g/L gamma-globulin suspended in 0.1 mol/L boric acid, pH 8.6. The incubation mixtures were centrifuged at 1,800 g for 20 minutes in order to separate the bound and free metabolites. The supernatant, which contained the bound metabolite, was decanted into a scintillation vial and counted in Bio-Safe II (Research Products International Corporation, Mount Prospect, Ill.). Duplicate incubations were made for each rat. Binding in the presence of 200 fold excess unlabeled 25-OHD$_3$ (non-specific binding) was subtracted from the total binding to obtain specific binding.

Protein: Urinary protein was measured by the bicinchoninic acid protein assay (Sigma-Aldrich, St. Louis, Mo.) according to the manufacturer's instruction, using an automated plate reader.

Statistical analyses: A mean±SEM was calculated for each group. Statistical significance was evaluated using two-way analysis of variance (ANOVA) followed by the Tukey multiple comparison test (SigmaStat, SPSS, Inc., Chicago, Ill.) The Mann-Whitney test was used for baseline comparisons, when rats were fed a non-purified diet.

Results:

In the set of studies, female S rats excreted 0.03±0.01 nmole 25-OHD/24 hours into urine at week 2 of low salt intake, whereas secretion by female R rats was non-detectable. Female S rats excreted 0.26±0.04 nmole 25-OHD/24 hours at week 2 of the high salt intake. This level was five times that of female R rats at week 2 of high salt intake (0.05±0.02 nmol/24 hours) and nine times that of S rats at week 2 of low salt intake.

The calculated 25-hydroxyvitamin D binding activity in the 24 hour urine of female S rats was 79±11 pmol/hour at week 2 of high salt intake, two times that in the urine of S rats at week 2 of low salt intake (33±10 pmol/hour) and greater than 35 times that in the urine of female R rats at week 2 of low (1.5±1.4 pmol/hour) of high salt intake (2.1±1.5 pmole/hour).

Urinary protein of S rats was significantly affected by salt (P<0.001) and by duration of high salt intake (P=0.05). Urinary protein of S rats was significantly higher than that of R rats during low (P=0.02) and high (P<0.001) salt intake Urinary 25-OHD was directly correlated (r=0.96, P<0.02) with urinary 25-hydroxyvitamin D binding activity during high salt intake.

The S rats excreted significantly higher urine volumes (P<0.001) than R rats during high salt intake, but similar urine volumes during low salt intake. Young female S rats are hypertensive at week 2 when fed a diet containing 80 g/kg salt.

It is seen that 25-hydroxyvitamin D binding activity in the urine of young female S rats was appreciable during low salt intake and doubled during high salt intake. The 25-OHD binding activity in the urine of young female R rats was non-detectable during low salt intake and detectable only at 1 week after start of the high salt intake, suggesting an adaptive mechanism in young female R rats. Higher excretion of 25-OHD binding activity by young S rats compared with young R rats is not related to urine volume during low salt intake, since urine volumes were similar. It is not known whether the increased excretion of 25-OHD and 25-OHD binding activity during high salt intake was caused by an acceleration of the mechanism during low salt intake or by an additional mechanism, such as kidney damage. Young S rats excreted significantly higher urine volumes than young R rats during high salt intake, suggesting altered kidney function.

Study of urinary 25-OHD binding activity in African-American men in a bed rest study: Healthy African-American men (29±2 years of age, 122±mm Hg, n=19) participated in a head-down tilt bed rest study done to determine excretion of 25-OHD binding protein(s) into the urine. The protocol involved low salt (50 mmol/day, 7 subjects) or high salt (200 mmol/day, 12 subjects) intake during seven days of head-down tilt bed rest. Plasma was collected at day 0 and day 7 and 24 hour and urine was collected at day 1 and day 7. Urinary sodium excretion of the subjects at day 1 suggests that sodium intake was high before the study. Urinary 25-OHD binding activity varied directly with urinary sodium (r=0.70, p<0.001), when sodium excretion was greater than 50 mmol/day. Urinary protein was also directly correlated with urinary sodium (r=0.56, p=0.0007). The mean baseline value for plasma 25-OHD concentration in the men was below that indicated as hypovitaminosis D (30 nmol/L) in other studies. (25-hydroxyvitamin D was detected in the urine of subjects in a study to determine urine volumes necessary for detection of 25-OHD in humans.) Significant urinary excretion of 25-OHD could account, in part, for low mean plasma 25-OHD concentration in some of these subjects.

Table 1. Relationship between urinary 25-OHD binding activity and urinary sodium for African American men engaged in a seven-day head-down tilt bed rest study.

| Sodium (range) (mmol/24 h) | Actual sodium (range) (mmol/24 h) | Total binding |
|---|---|---|
| 51–100 (n = 1) | 82 | 451 |
| 101–150 (n = 4) | 131 +/– 11 | 878 =/– 264 |
| 151–200 (n = 10) | 180 +/– 15 | 1287 +/– 856 |
| 201–250 (n = 5) | 230 +/– 10 | 1674 +/– 479 |
| 251–300 (n = 2) | 264 +/– 7 | 2043 +/– 402 |
| 301–350 (n = 1) | 305 | 2125 |
| 400–450 (n = 1) | 421 | 3355 |

Results of this study showed 25-OHD binding activity in these men varied directly with urinary sodium.

The use of the bed rest subjects to study the urinary loss of 25-OHD and 25-OHD binding proteins presents some limitations, in that bed rest may affect excretion. Studies with hind limb unloaded (a space flight model) S rats indicate greater 25-OHD binding activity in the urine of the unloaded rats than in the urine of control rats when the rats were fed 2% salt, an intake designed to mimic high salt intake in humans.

Urinary 25-OHD binding activity in young normotensive and hypertensive men: Urine samples from ambulatory men (20-29 years old) were obtained from Clinomics Biosciences Inc. (Pittsfield, Mass.) in order to determine the feasibility of using urinary 25-OHD binding activity as a marker of salt sensitivity. The subjects were well-matched by age and, based on urinary sodium, were on high salt diets. All hypertensive subjects were on medication for hypertension.

Urinary protein/sodium was significantly higher for normotensive African-Americans than for normotensive Caucasian Americans. Urinary protein did not significantly differ between normotensive and hypertensive African-Americans. A significant correlation between urinary protein and urinary sodium was observed only for normotensive Caucasians, the group with the lowest mean protein excretion.

Significant correlation between urinary vitamin D binding activity and urinary sodium was observed only for hypertensive African-Americans. (The prevalence of salt sensitivity in hypertensive African-Americans has been reported to be approximately 70%.)

Table 2. Urinary 25-OHD binding activity/urinary sodium for normotensive (N) and hypertensive (H) African-American (AA) and Caucasian (C) subjects

| Characteristic | 25-OHD binding/ sodium (pmol/h-mmol) | | |
|---|---|---|---|
| | Mean | Median | Range |
| C-N (n = 10) | 2.0 +/– 0.6 | 1.4 | 0–5.7 |
| C-H (n = 10) | 2.5 +/– 0.5 | 1.8 | 0.9–7.4 |
| AA-N (n = 10) | 2.5 +/– 0.3 | 2.2 | 1.3–4.1 |
| AA-H (n = 10) | 2.3 +– 0.2 | 2.3 | 1.4–3.2 |

Although there were no differences in mean urinary binding activity/sodium, the median values showed a stepwise increase with African-Americans having the highest medians, and the African-American hypertensive group having a higher median than the African-American normotensive group. Caucasians showed a much wider range of values.

If one sets a cut-off of >2.5 pmol/hr-mmol for binding activity/sodium (mean for normotensive African-Americans), one obtains a salt sensitivity prevalence of 40% for normotensive and hypertensive African-Americans and 30% for normotensive and hypertensive Caucasians. The low percentage for hypertensive African-Americans may be due to their use of medication.

Study in senile rats: A study was done on 12 month-old male S rats fed a standard (1% salt) diet who were suffering from nephrosclerosis and cardiac hypertrophy and who exhibited low plasma 25-OHD concentrations. The rats were fed a standard diet (1% salt), then switched to an 0.3% or 2% salt diet three weeks prior to sacrifice. When compared with R rat controls, kidneys of the S rats were enlarged and showed extensive nephrosclerosis and tubular atrophy, which was lacking in the R rats of the same age. Salt sensitivity, thus, appears to induce accelerated cardiovascular aging. The S rats had exceedingly low 25-OHD concentrations. There was significant 25-OHD, 25-OHD-binding activity and protein in the urine of the S rats (three times that in the urine of R rats) which probably contributed to the low plasma 25-OHD concentrations in the S rats. The calcium endocrine system of the S rats fed 2% salt three weeks prior to sacrifice was similar to that found in elderly humans with low renin hypertension.

In view of the above, it is clear that it is possible to evaluate salt sensitivity of an individual by comparing the amount of 25-OHD or 25-OHD binding activity in the urine. Measurement of 25-OHD binding activity is easier and requires only labeled and unlabeled 25-OHD. An easy automatic urinary sodium determination can normalize the data. The non-intrusive and economical nature of this test clearly renders the instantly disclosed procedure of great value in the clinical setting. Though testing of 25-OHD in the urine would provide an alternative test, far more urine is required.

Summarizing, the essential steps required to evaluate 25-OHD binding activity in the urine to determine whether an individual is salt-sensitive requires:

(a) collecting a urine sample from said individual and (b) preparing samples containing a known amount of radiolabeled 25-hydroxyvitamin $D_3$, (c) preparing two sets of samples (1) by adding to some of the samples obtained in step (b) a known amount of 25-hydroxyvitamin $D_3$ (designated 25-OHD samples)

(2) retaining the second set of the samples obtained in step (b) without addition of 25-hydroxyvitamin $D_3$ (designated non-25-OHD samples)

(d) incubating all samples, (e) measuring the amount of radioactivity in each sample, and (f) determining the amount of activity in any sample by subtracting the counted level of activity in 25-OHD samples (samples (1)) from the amount of activity in the samples to which no 25-OHD (the non-25-OHD) (samples (2)) has been added, to obtain specific binding.

While specific buffers and conditions for cleaning/clearing the samples have been described, variations in such standard procedures are known to those in the art and such variations may be practiced without altering the determinative outcome of the testing.

What we claim is:

1. A method for determining salt sensitivity in an individual comprising:
   (1) adding a known amount of radiolabeled 25-hydroxyvitamin $D_3$ to a first aliquot of a urine sample from an individual and to a second aliquot of the same urine sample, and adding a known amount of unlabeled 25-hydroxyvitamin $D_3$ to the first aliquot;
   (2) incubating the first and the second aliquots prepared in step (1) to allow radiolabeled 25-hydroxyvitamin $D_3$ binding to proteins in the urine;
   (3) precipitating the unbound radio labeled 25-hydroxyvitamin $D_3$;
   (4) measuring the radioactivity in the supernatant of each aliquot of step (3);
   (5) comparing the radioactivity in the first aliquot with the radioactivity in the second aliquot, wherein an excess of radioactivity in the second aliquot over the radioactivity in the first aliquot is deemed indicative of 25-hydroxyvitamin $D_3$ binding activity in the urine sample,
   wherein a higher-than-normal 25-hydroxyvitamin $D_3$ binding activity in the urine is indicative of salt sensitivity or predisposition to salt-associated hypertension.

2. A method of determining specific 25-hydroxyvitamin $D_3$ binding activity in a urine sample comprising the steps of:
   (1) adding a known amount of radiolabeled 25-hydroxyvitamin $D_3$ to two or more identical samples of urine from an individual and a known amount of excess unlabeled 25-hydroxyvitamin $D_3$ to half of the samples to compete with the radiolabeled 25-hydroxyvitamin $D_3$ for binding proteins in the urine;
   (2) incubating all samples prepared in step (1) to allow radiolabeled 25-hydroxyvitamin $D_3$ binding to proteins in the urine;
   (3) incubating samples prepared in step (2) in buffered dextran-coated charcoal, then centrifuging to precipitate the unbound radio labeled 25-hydroxyvitamin $D_3$;
   (4) measuring the average radioactivity in the supernatant of each sample of step (3);
   (5) comparing the average radioactivity in the samples containing excess unlabeled 25-hydroxyvitamin $D_3$ with those to which no unlabeled 25-hydroxyvitamin $D_3$ had been added to determine 25-hydroxyvitamin D binding proteins in the urine sample, wherein an excess of average radioactivity in the samples which lacked unlabeled 25-hydroxyvitamin $D_3$, over the average radioactivity of samples which contain excess unlabeled 25-hydroxy vitamin $D_3$ is deemed indicative of 25-hydroxyvitamin $D_3$ binding activity in the urine sample,
   wherein a higher-than-normal 25-hydroxyvitamin $D_3$ binding activity in the urine is deemed indicative of salt sensitivity or predisposition to salt-associated hypertension.

3. The method of claim 2, wherein the sample tested is human urine

* * * * *

UNITED STATES PATENT AND TRADEMARK OFFICE
CERTIFICATE OF CORRECTION

| | | |
|---|---|---|
| PATENT NO. | : 7,888,000 B2 | |
| APPLICATION NO. | : 10/617254 | |
| DATED | : February 15, 2011 | |
| INVENTOR(S) | : Myrtle Thierry-Palmer | |

It is certified that error appears in the above-identified patent and that said Letters Patent is hereby corrected as shown below:

Title Page, Item (56)
    "Other Publications", line 2, after "Biochem" please delete "ol" and insert --Mol.--;
    "Other Publications", line 5, after "Physiol" please delete "200" and insert --2000--;
    "Other Publications", line 7, delete "Nurtrition" and insert --Nutrition--.

Column 1, line 41, change "salt-sensitive" to --salt sensitivity--;
    line 59, change "mein" to --mean--.

Column 2, line 23, change "(non25-OHD)" to --(non-25-OHD)--.

Column 3, line 1, after "required 25-OHD" please insert --,--;
    line 1, change "radiolabelled" to --radiolabeled--;
    line 4, please delete "," after "Amersham";
    line 19, change "Animal Diets" to --Animal and diets--;
    line 24, delete "," after the word "tional";
    line 41, delete "/" after the word "mol";
    line 43, change "25 Hydroxy[26(27)" to --25-Hydroxy[26(27)--;
    line 48, change "25 Hydroxyvitamin..." to --25-Hydroxyvitamin...--;
    line 51, change "25 OHD" to --25-OHD--;
    line 56, change "25 OHD" to --25-OHD--;
    line 57, change "0,078, 0,312" to --0.078, 0.312--;
    line 58, change "25 ng/tube" to --2.5 ng/tube--;
    line 61, change "25-hydroxyvitamin" to --25-Hydroxyvitamin--; and
    line 64, change "185 (1986)" to --185, 1986--.

Column 4, line 15, change "200 fold" to --200-fold--;
    line 25, change "SPSS," to --SPSS--;
    line 29, change "female" to --Female--;
    line 42, change "of high salt" to --or high salt--; and Signed and Sealed this
Twelfth Day of April, 2011

David J. Kappos
*Director of the United States Patent and Trademark Office*

CERTIFICATE OF CORRECTION (continued)
U.S. Pat. No. 7,888,000 B2 line 59, change "1" to --one--.

Column 5, line 12, change "24 hour and urine" to --24 hour urine--;
        line 16, change "p<0.001)" to --P<0.001)--;
        line 18, change "p<0.001)" to --P<0.001)--;
        line 21, change "25-hydroxyvitamin" to --25-Hydroxyvitamin--; and
        line 36, change "878=/-264" to --878+/-264--.

Column 6, line 17, change "2.3 +-0.2" to --2.3 +/-0.2--; and
        line 54, change "automatic" to --automated--.

Column 7, line 8, change "sample, supernatant" to --sample supernatant--; and
        line 33, change "radio labeled" to --radiolabeled--.

Column 8, line 19, change "radio labeled" to --radiolabeled--;
        line 30, change "25-hydroxy vitamin" to --25-hydroxyvitamin--; and
        line 30, change "vitamin $D_3$", please insert --vitamin $D_3$,--.